(12) United States Patent
Radocy

(10) Patent No.: US 8,984,736 B2
(45) Date of Patent: Mar. 24, 2015

(54) PROSTHETIC DEVICE FOR HANDLING A BALL

(75) Inventor: Robert Radocy, Boulder, CO (US)

(73) Assignee: Therapeutic Recreation Systems, Inc., Boulder, CO (US)

( * ) Notice: Subject to any disclaimer, the term of this patent is extended or adjusted under 35 U.S.C. 154(b) by 123 days.

(21) Appl. No.: 13/572,503

(22) Filed: Aug. 10, 2012

(65) Prior Publication Data

US 2014/0041188 A1 Feb. 13, 2014

(51) Int. Cl.
*B23P 11/00* (2006.01)
*B23P 17/00* (2006.01)
*B25B 1/00* (2006.01)
*A63B 59/00* (2006.01)
*A63B 59/02* (2006.01)
*A61F 2/58* (2006.01)

(52) U.S. Cl.
CPC ............ *A61F 2/588* (2013.01); *Y10T 29/49826* (2015.01)
USPC .................. 29/525.01; 29/525.11; 29/525.13; 269/71; 269/75; 473/510; 473/513

(58) Field of Classification Search
CPC ... A61F 2220/0041; A61F 2/54; A61F 2/586; A61F 2/585; A61F 2/583; A61F 2/58; A61F 2/588; F41B 3/04; F41B 3/00; A63B 53/14; A63B 59/0014; A63B 47/02; A63B 59/025; A63B 59/0025; A63B 49/08; A63B 59/02; B21C 37/151
USPC ............. 29/525.01, 525.11, 525.13; 473/510, 473/553, 286, 513; 124/5; 623/57, 65, 623/61–63; 269/71, 75, 79, 3, 6
See application file for complete search history.

(56) References Cited

U.S. PATENT DOCUMENTS

| | | | | |
|---|---|---|---|---|
| 1,826,651 | A | * | 10/1931 | Chisholm ...................... 425/221 |
| 2,122,984 | A | * | 7/1938 | Loomis .............................. 124/5 |
| 2,364,313 | A | * | 12/1944 | Pecorella ......................... 623/64 |
| 2,540,375 | A | * | 2/1951 | Motis ............................... 623/64 |
| RE23,761 | E | * | 12/1953 | Sarvie ............................... 81/323 |
| 3,170,688 | A | * | 2/1965 | Porter ........................... 473/503 |
| 3,589,349 | A | * | 6/1971 | Parker .............................. 124/5 |
| 3,747,128 | A | * | 7/1973 | De Filipo ........................ 623/65 |
| 3,802,302 | A | * | 4/1974 | Bengtson ..................... 81/177.2 |
| 4,233,952 | A | * | 11/1980 | Perkins ............................. 124/5 |
| 4,548,413 | A | * | 10/1985 | David ........................... 473/173 |
| 4,661,113 | A | * | 4/1987 | Adkins ........................... 623/65 |
| 4,834,760 | A | * | 5/1989 | Richter, Jr. ...................... 623/65 |
| 4,865,613 | A | * | 9/1989 | Rizzo ............................. 623/65 |
| 4,944,765 | A | * | 7/1990 | Keith .............................. 623/65 |
| 4,990,162 | A | * | 2/1991 | LeBlanc et al. ................. 623/63 |
| 5,013,326 | A | * | 5/1991 | Horvath .......................... 623/64 |
| 5,085,665 | A | * | 2/1992 | Radocy et al. .................. 623/57 |
| 5,116,386 | A | * | 5/1992 | Scribner ......................... 623/64 |
| 5,463,942 | A | * | 11/1995 | Hupf et al. ...................... 99/537 |
| 5,476,297 | A | * | 12/1995 | Lombard ..................... 294/19.2 |
| 5,551,690 | A | * | 9/1996 | Brown .......................... 473/538 |
| 5,800,572 | A | * | 9/1998 | Loveall .......................... 623/63 |
| 5,888,235 | A | * | 3/1999 | Jacobsen et al. ............... 623/58 |

(Continued)

*Primary Examiner* — David Bryant
*Assistant Examiner* — Bayan Salone
(74) *Attorney, Agent, or Firm* — Craig R. Miles; CR MILES, P.C.

(57) ABSTRACT

A prosthetic device which couples to the remaining portion of a limb of an amputee which provides a ball handling structure including a ball handling surface which defines an opening through which a ball passes into and out of a ball receiving cavity allowing the ball to be handled by the amputee.

19 Claims, 13 Drawing Sheets

(56) References Cited

U.S. PATENT DOCUMENTS

| | | | |
|---|---|---|---|
| 6,076,829 A * | 6/2000 | Oblack | 273/317 |
| 6,216,640 B1 * | 4/2001 | Zelinger | 119/707 |
| 6,378,219 B1 * | 4/2002 | Hatlee | 30/391 |
| 6,416,555 B1 * | 7/2002 | Dillenburg et al. | 623/65 |
| 6,460,254 B1 * | 10/2002 | Mori et al. | 30/286 |
| 6,485,523 B2 * | 11/2002 | Pierce et al. | 623/65 |
| 6,582,473 B2 * | 6/2003 | Pierce et al. | 623/65 |
| 7,032,583 B1 * | 4/2006 | Hall | 124/5 |
| 7,087,092 B1 * | 8/2006 | Landsberger | 623/57 |
| 7,677,994 B2 * | 3/2010 | Matsumoto et al. | 473/510 |
| 7,686,001 B2 * | 3/2010 | Fitt | 124/5 |
| 8,015,968 B2 * | 9/2011 | Christ | 124/5 |
| 8,021,435 B2 * | 9/2011 | Bravo Castillo | 623/64 |
| D655,359 S * | 3/2012 | Thorogood | D21/722 |
| 8,246,480 B2 * | 8/2012 | Parks et al. | 473/226 |
| 8,302,585 B2 * | 11/2012 | FitzGerald | 124/5 |
| 8,418,681 B2 * | 4/2013 | Levin et al. | 124/5 |
| 8,517,003 B2 * | 8/2013 | Fisher | 124/5 |
| 8,523,699 B2 * | 9/2013 | Bennett | 473/286 |
| 8,539,939 B2 * | 9/2013 | Minneman et al. | 124/5 |
| 8,720,385 B2 * | 5/2014 | Tanner | 119/796 |
| 8,801,534 B1 * | 8/2014 | Rydberg | 473/286 |
| 2004/0248676 A1 * | 12/2004 | Taylor et al. | 473/513 |
| 2005/0263962 A1 * | 12/2005 | Roh et al. | 273/317 |
| 2006/0229136 A1 * | 10/2006 | Presley | 473/157 |
| 2007/0049396 A1 * | 3/2007 | Scheibe | 473/282 |
| 2007/0191131 A1 * | 8/2007 | Nickel | 473/285 |
| 2007/0259731 A1 * | 11/2007 | Barouh | 473/282 |
| 2008/0004140 A1 * | 1/2008 | Matsumoto et al. | 473/513 |
| 2008/0308086 A1 * | 12/2008 | Wessells et al. | 124/5 |
| 2012/0048251 A1 * | 3/2012 | Oblack et al. | 124/5 |

* cited by examiner

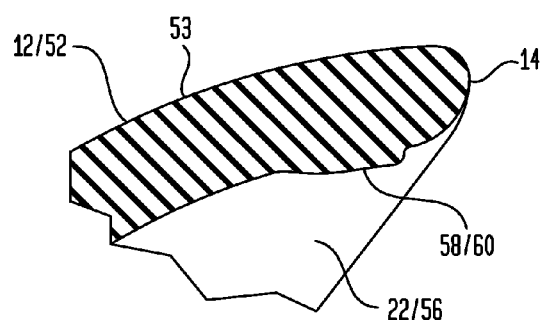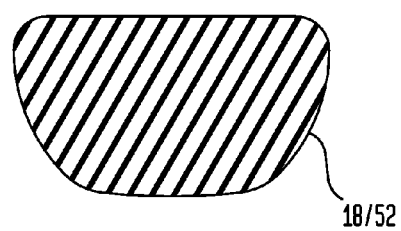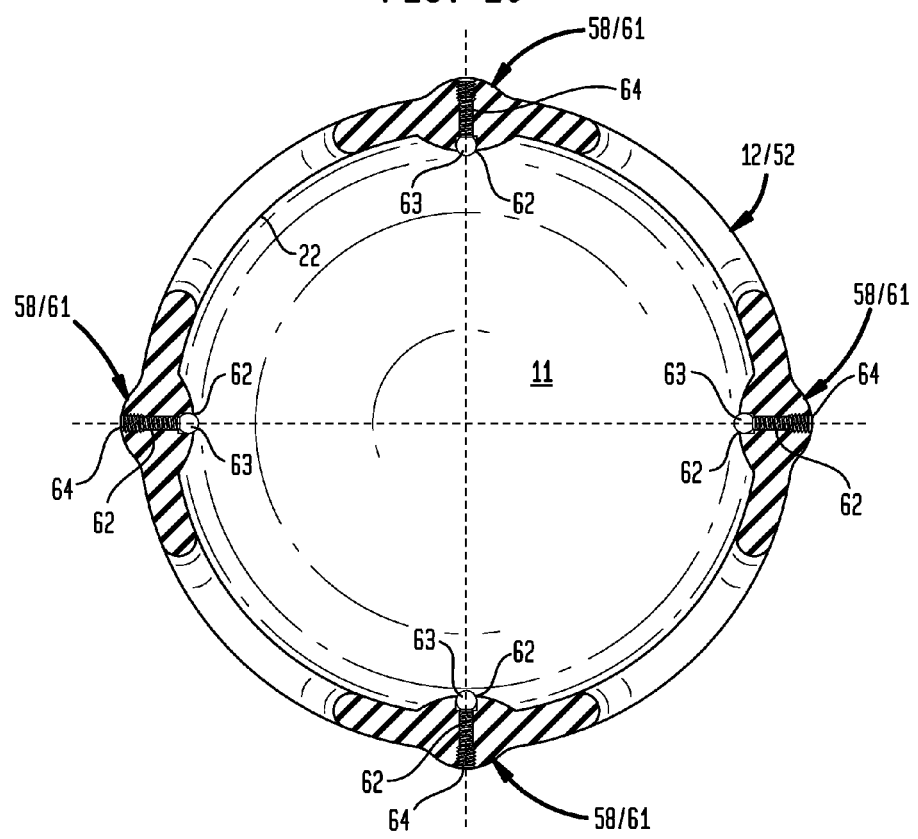

PROSTHETIC DEVICE FOR HANDLING A BALL

I. FIELD OF THE INVENTION

A prosthetic device which couples to the remaining portion of a limb of an amputee which provides a ball handling structure including a ball handling surface which defines an opening through which a ball passes into and out of a ball receiving cavity allowing the ball to be handled by the amputee.

II. BACKGROUND OF THE INVENTION

There are a numerous and wide range of prosthetic devices which can be coupled to the remaining portion of the limb of an amputee. However, until the instant invention, there remained a long felt and unresolved need for a prosthetic device for handling a ball. This may be due to a variety of unresolved difficulties in the provision of a prosthetic structure for ball handling.

In the first instance, conventional prosthetic devices do not allow both retention of a ball unaided by another limb and also release of the ball in response to a substantially normal range of throwing movements of the remaining portion of a limb of an amputee.

Another difficulty involves provision of a prosthetic structure for handling a ball adjustable in the first instance to the lengths of the remaining limbs in a population of amputees and in the second instance to the range of throwing movements of the remaining portion of a limb of each particular amputee.

Another difficulty involves provision of a prosthetic structure for handling a ball which has an amount of flexure in response the mass and type of the ball being handled adjustable to aid in release of the ball from the prosthetic structure.

Another difficulty involves provision of a prosthetic device having a structure which allows the amputee to control the travel path of the ball toward a target based on a substantially normal range of throwing movements of the remaining portion of the limb of the amputee.

Another difficulty involves provision of a prosthetic device having a structure which allows the amputee to control the velocity of the ball in a travel path toward a target over a relative broad velocity range from a few miles per hour to over 40 miles per hour or even greater.

III. SUMMARY OF THE INVENTION

Accordingly, a broad object of the invention can be to provide embodiments of a prosthetic device for handling a ball which provides an attachment portion which can be coupled to the socket or other interface which engages the remaining portion of the limb of an amputee, a support member coupled to the attachment portion which extends a distance outward of the attachment portion, and a ball handling structure coupled to the support member which provides a ball handling surface configured to engage, retain and release a wide range of ball configurations by the movement of the remaining portion of the limb of an amputee.

Another broad object of the invention can be to provide a method of producing a prosthetic device by providing an attachment portion configured to couple the prosthetic device to an amputee, coupling a support member having a length disposed between a support first end and a support second to the attachment portion by the support first end, and coupling a ball handling structure to the support second end, the ball handling structure having a ball handling surface configured to engage a ball to retain and allow release of the ball in response to movement of the remaining portion of the limb of an amputee.

Another broad object of the invention can be to provide a method of handling a ball by obtaining a prosthetic device which includes an attachment portion configured to couple to an amputee, an support member coupled to the attachment portion, and a ball handling structure coupled to the support member which includes a ball handling surface configured to engage a ball, and coupling the prosthetic device to the remaining portion of a limb of an amputee, and engaging a ball with the ball handling surface.

Naturally, further objects of the invention are disclosed throughout other areas of the specification, drawings, photographs, and claims.

IV. BRIEF DESCRIPTION OF THE DRAWINGS

FIG. 18 is a cross section view 18-18 shown in FIG. 4 of a particular embodiment of a ball retention element.

FIG. 19 is a cross section view 19-19 shown in FIG. 6 of a particular embodiment of a support member.

FIG. 20 is a cross section view 20-20 shown in FIG. 6 of a particular embodiment of a ball handling structure.

V. DETAILED DESCRIPTION OF THE INVENTION

Figure 1:
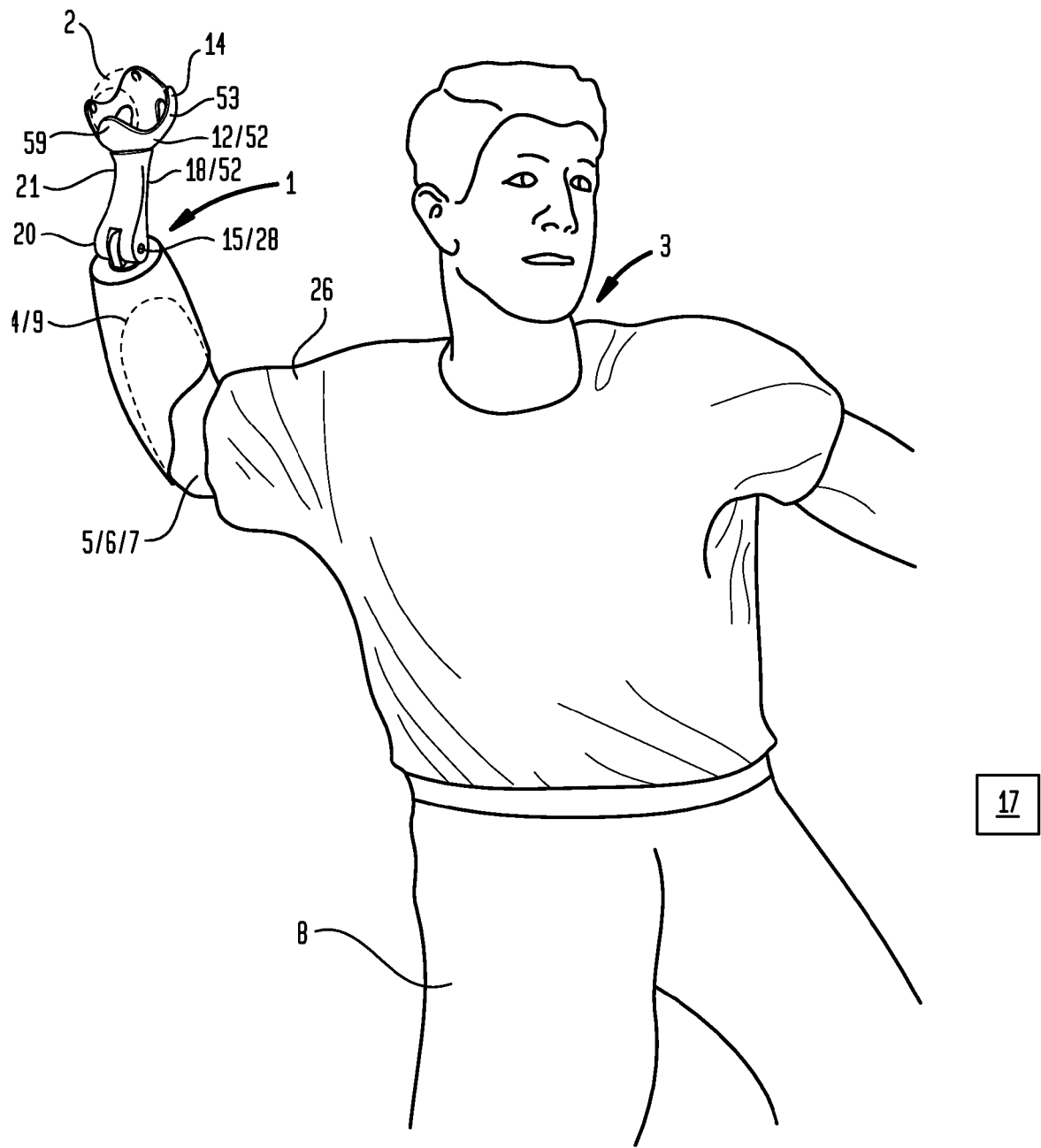
FIG. 1 is an illustration of a method of handling a ball with a particular embodiment of the inventive prosthetic device.

Now referring primarily to FIGS. 1 through 4, which illustrates a method of using a particular embodiment of the inventive prosthetic device (1) for handling a ball (2). For the purposes of this invention the term "ball" means an object having a body composed of one or more materials whether hollow or solid which can be, but is not limited to, a spherical form, with examples including: a baseball, as softball, tennis ball, golf ball, a pickle ball, a wiffle ball, or the like. An amputee (3) can obtain an embodiment of the prosthetic device (1) which includes an attachment portion (4) which can be coupled to a remaining portion (5) of a limb (6). For the purposes of this invention the term "amputee" means a person lacking a portion of a limb whether a result of amputation or congenital disorder. For the purposes of this invention, the term "limb" means an arm (7) or a leg (8). The term "coupled to" means any manner of attachment of the prosthetic device (1) to the amputee (3), and without limitation to the breadth of the forgoing, can include attachment of the prosthetic device (1) by way of an interface in the form of a socket (9) which receives the remaining portion (5) of the limb (6) and which may also include a frame and suspension, or an interface including an abutment coupled to an implant osseointegrated with the bone at the terminal end (10) of the remaining portion (5) of the limb (6).

Upon attachment of the prosthetic device (1), the amputee (3) can position a ball (2) inside of a ball receiving cavity (11) of a ball handling structure (12). As to certain embodiments of the prosthetic device (1), the amputee (3) can sufficiently forcibly urge the ball (2) against an opening (14) having lesser dimension than the ball (2) thereby generating sufficient flexure in the ball handling structure (12) to allow the ball (2) to pass through the opening (14) into the ball receiving cavity (11). As to particular embodiments, the amputee (3) can further adjust orientation of the opening (14) in the ball handling structure (11) in relation to the attachment portion (4) by rotating the ball handling structure (11) about a first pivot element (15) or about a second pivot element (16) (or about both the first pivot element (15) and the second pivot element (16)).

As to certain embodiments, the amputee (3) can generate sufficient motion in the prosthetic device (1) by movement of the remaining portion (5) of the limb (6) to release the ball (2) from the ball handling structure (12). Adjustment of orientation of the ball handling structure (12) coordinated with controlled motion of the prosthetic device (1) allows the amputee (3) to control the travel path of the ball (2) toward a target (17).

Figure 2:
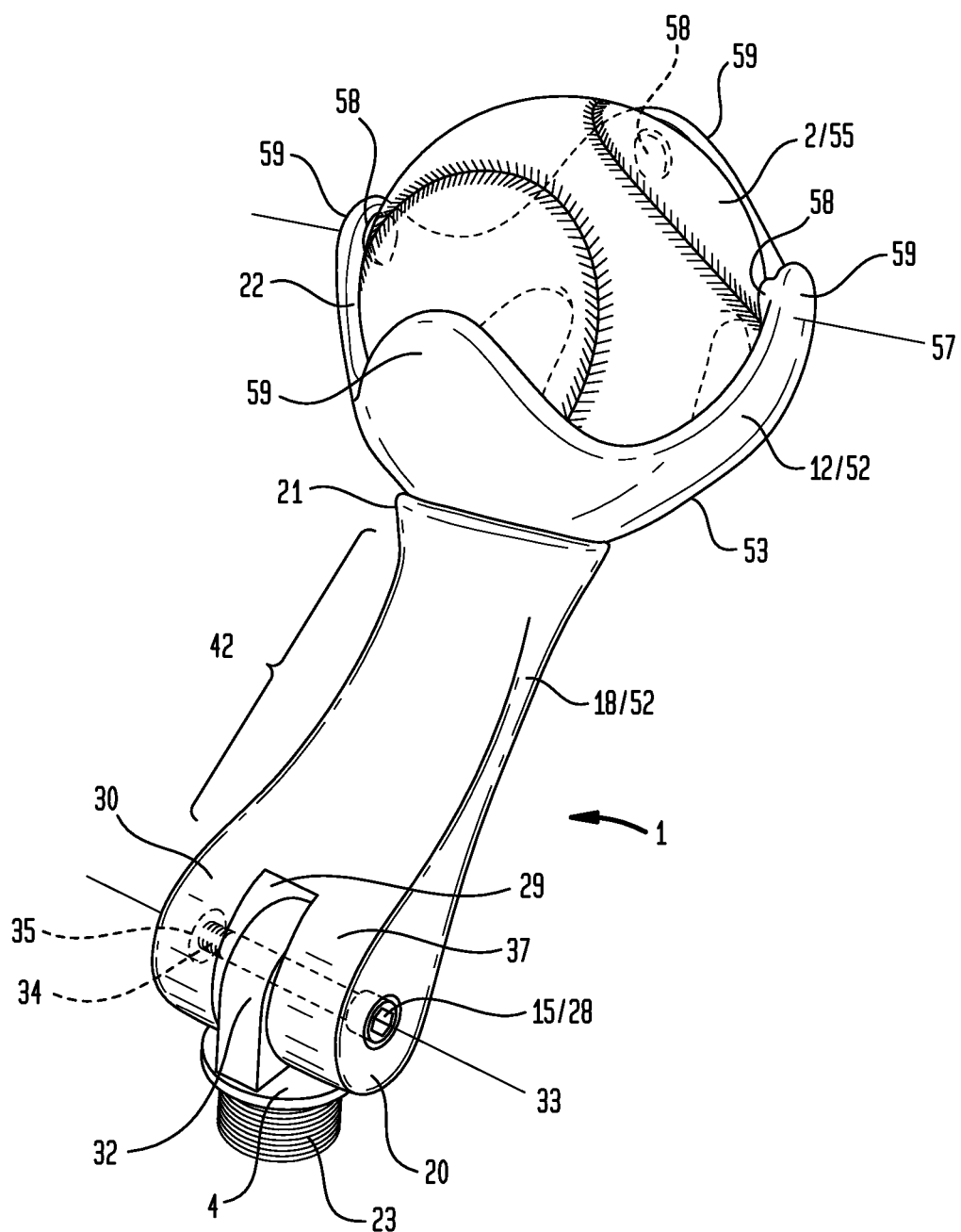
FIG. 2 is perspective view of a particular embodiment of the inventive prosthetic device engaged to a particular type of ball.
Figure 3A:
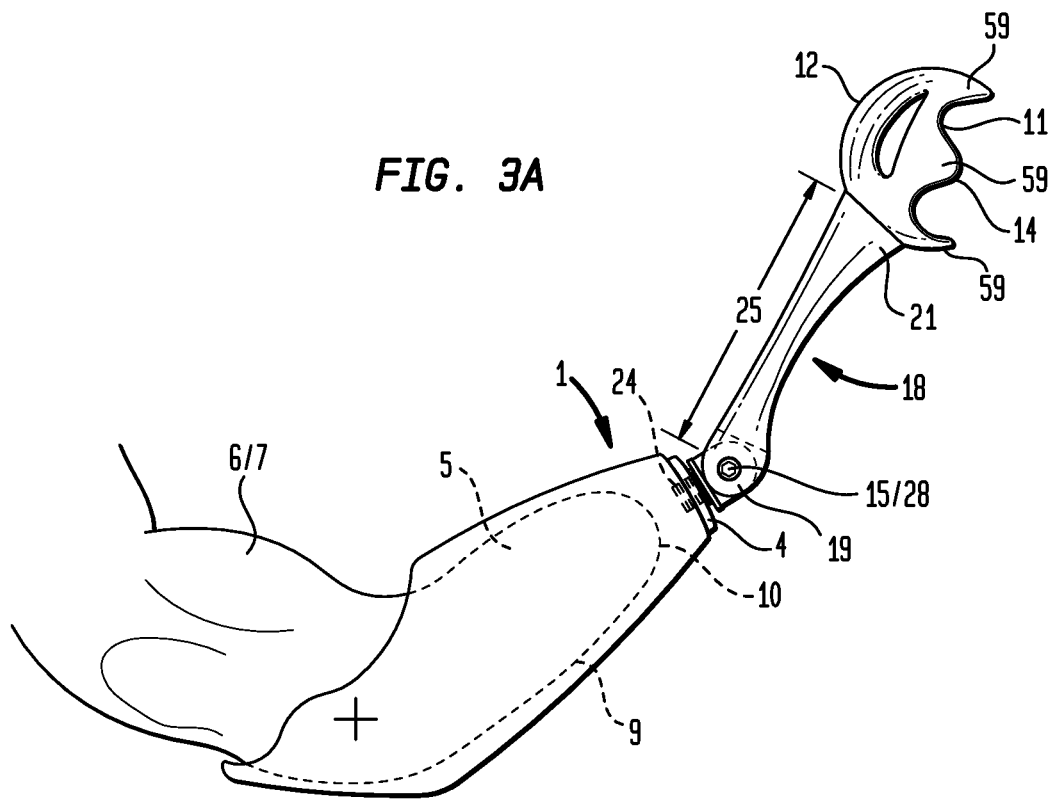
FIG. 3A is a side view of a particular embodiment of an attachment portion for coupling embodiments of the inventive prosthetic device to the remaining portion of a limb of an amputee.
Figure 3B:
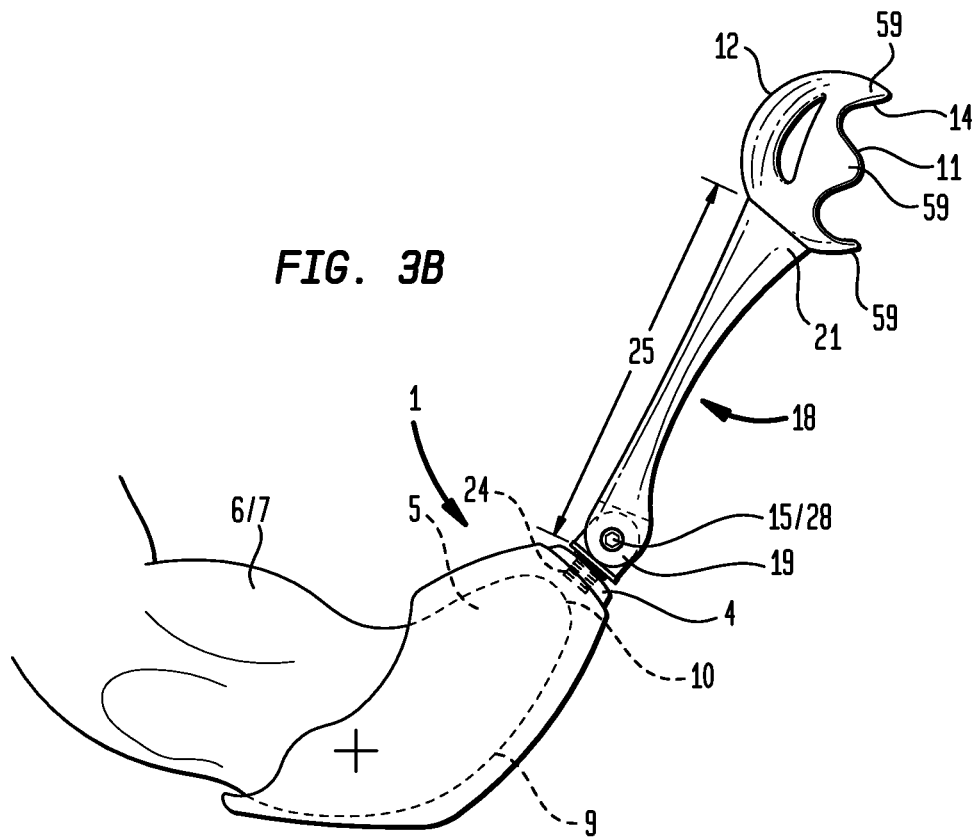
FIG. 3B is a side view of a particular embodiment of an attachment portion for coupling embodiments of the inventive prosthetic device to the remaining portion of a limb of an amputee.

Now referring primarily to FIGS. 2 and 3A and 3B, the structure of the prosthetic device (1) can include an attachment portion (4) configured to couple to an amputee (3), a support member (18) coupled to the attachment portion (4), and a ball handling structure (12) coupled to the support member (18).

In the particular embodiment shown in FIGS. 2, 3A and 3B, the attachment portion (4) includes a socket (9) (as shown in the examples of FIGS. 3A and 3B) and a spirally threaded member (23) (as shown in the example of FIG. 2) which rotationally mates with a spirally threaded recess (24) of the socket (9) to allow disconnect of the support member (18) and ball handling structure (12) from the socket (9) or other interface; however, embodiments of the attachment portion (4) broadly encompass any manner of coupling of the support member (18) to the remaining portion (5) of a limb (6) of an amputee (3) and the spirally threaded member (23) and the spirally threaded recess (24) can as to particular embodiments comprise a universal coupler which allows rapid disconnect of the support member (18) and ball handling structure (12) from the socket (9) or other interface. As to particular embodiments of the prosthetic device (1) for ball handling, the attachment portion (4) may not provide the socket (9) or other interface which an amputee (3) may already own, but may provide a spirally threaded member (23), universal coupler, or other configuration of coupler to secure the support member (18) and ball handling structure (12) to the existing socket (9) or other interface.

Now referring primarily to FIGS. 3A and 3B, depending upon the length of the remaining portion (5) of the limb (6), the configuration of the attachment portion (4) can vary along with the length (25) of the support member (18) to provide a prosthetic device (1) which maintains a similar spatial relationship between the ball handling structure (12) and the shoulder (26) of the amputee (3) even when the length of the remaining portion (5) of the limb (6) varies.

Figure 16A:
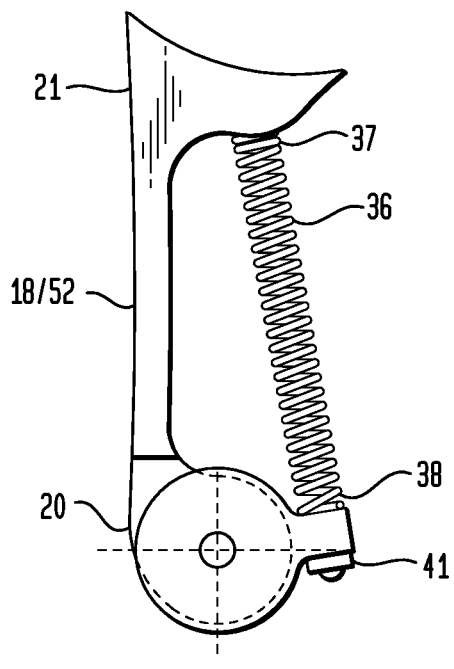
FIG. 16A is a side view of a particular embodiment of a support member.
Figure 16B:
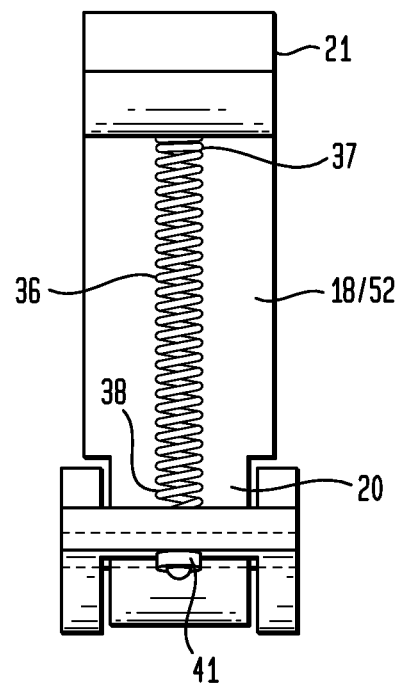
FIG. 16B is a front view of a particular embodiment of a support member.

Now referring primarily to FIGS. 2, 4 through 8, the support first end (20) can be coupled to the attachment portion (4) in fixed relation, or in pivotally coupled rotational relation which can be variably positionally fixed (as shown in the example of FIGS. 4 through 8) or pivotally coupled rotational relation which can be variably tensioned (as shown in the example of FIGS. 16 A and 16 B). As to particular embodiments, the support first end (20) can be pivotally coupled to the attachment portion (4) to allow the support member (18) to rotationally travel about a first pivot element (15). As to certain embodiments a support lock (28) can operate to act upon the support first end (20) to positionally fix the support member in relation to the attachment portion (4).

As shown in the embodiment shown in FIGS. 4 through 8, the support first end (20) can afford a flange receiving slot (29) between bifurcate members (30)(31). A flange (32) extending from the attachment portion (4) can be located in the flange receiving slot (29). The first pivot element (15) can be disposed in the bifurcate members (30)(31) to pass through the flange (32) providing an first axis (33) about which the support member (18) rotates. The first pivot element (15) can be in the form of a mechanical fastener having a spirally threaded shaft (34) which mates with a spirally threaded recess (35) disposed in one of the bifurcate members (30) to provide the support lock (28). Rotation of the spirally threaded shaft (34) can dispose the bifurcate members a sufficient lesser distance apart to forcibly engage the external surface of the flange (32) to fix orientation of the support member (15) in relation to the attachment portion (4).

As shown in the embodiment of FIGS. 16A and 16 B, the support first end (20) can be pivotally coupled to the attachment portion (4). A spring element (36) can be coupled by opposed spring ends (37)(38) between the attachment portion (4) and the support member (18). Upon rotation of the support member (18) from a first position (39) toward a second position (40) the spring element (36) mechanically deforms and assists in returning the support member (18) toward the first position (39). As to particular embodiments, a spring tensioner (41) can operate to generate a variable amount of tension in the spring element (36) to increase resistance to rotation of the support member (18) about the first pivot element (15). As to the embodiment shown in the Figures the spring element (36) can take the form of a coil spring. However, for the purposes of this invention the term "spring element" means any elastic element which stores energy upon mechanical deformation and releases the energy in returning to the relaxed condition.

Figure 9:
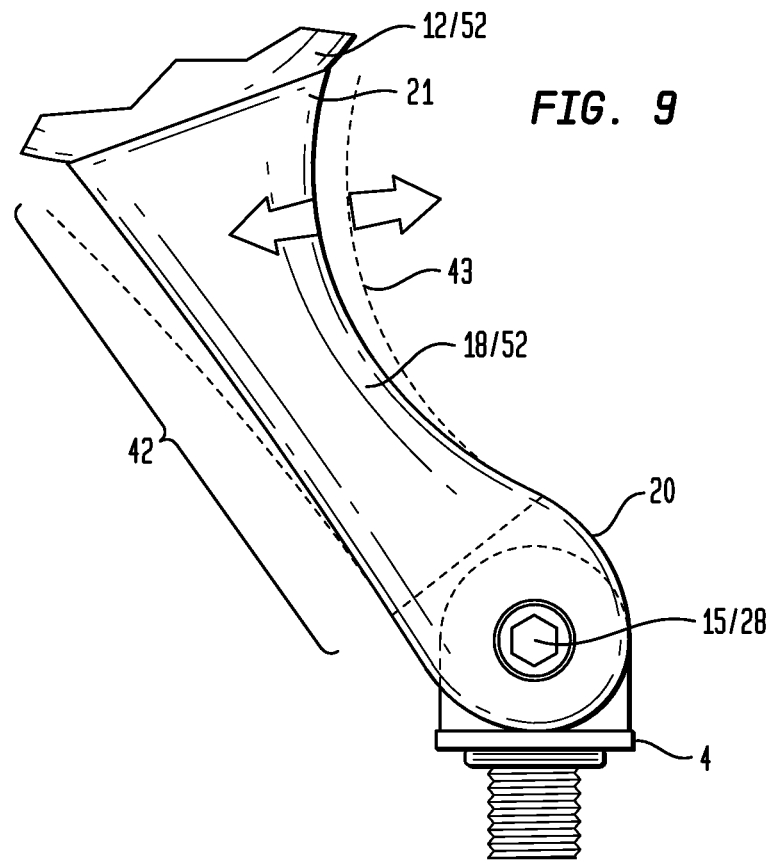
FIG. 9 is a partial side view of a particular embodiment of the inventive prosthetic device for handling a ball showing an amount of flexure of a support member.

Now referring primarily to the embodiments of the support member (18) shown in FIGS. 2, 4 through 10, 12A and 12B, 13A and 13B, 14A and 14B, and 15, the support member (18) can be produced by fabrication or molded from a variety of elastomeric materials (52) and combinations thereof whether as thermosets or thermoplastics which can reversibly extend from about 5% to about 700% depending on the formulation. Examples of elastomer materials (52) include: polyurea, polyurethane, polyisoprene, poly butadiene, chloropene, nitrile rubber, ethylene propylene rubber, thermoplastic elastomer, or the like. The support member (18) can have a medial portion (42) disposed between the support first end (20) and the support second end (21) which can be produced using various combinations of elastomeric materials (52) and in various configurations depending upon the mass and configuration of the ball (2) to be retained in the ball handling structure (12) and the amount of resilient flexure (43) (as shown in the example of FIG. 9) to achieve in the support member (18) in response to movement of a particular mass and configuration of the ball (2).

Figure 10:
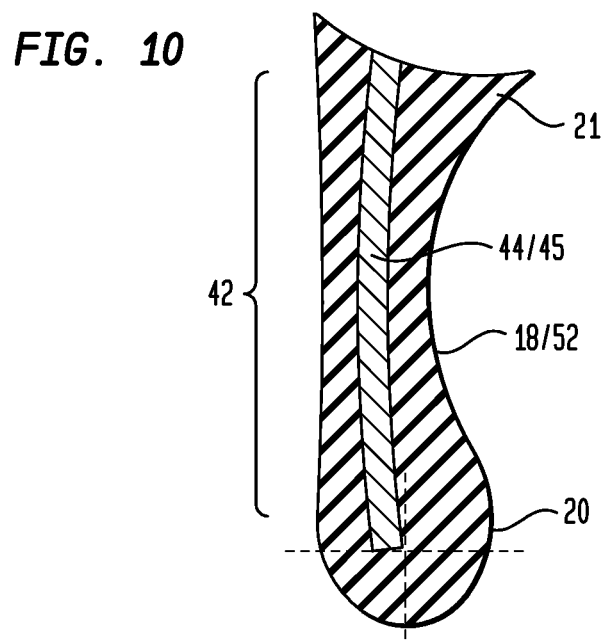
FIG. 10 is a cross section view 10-10 shown in FIG. 5 of a particular embodiment of a support member.
Figure 11:
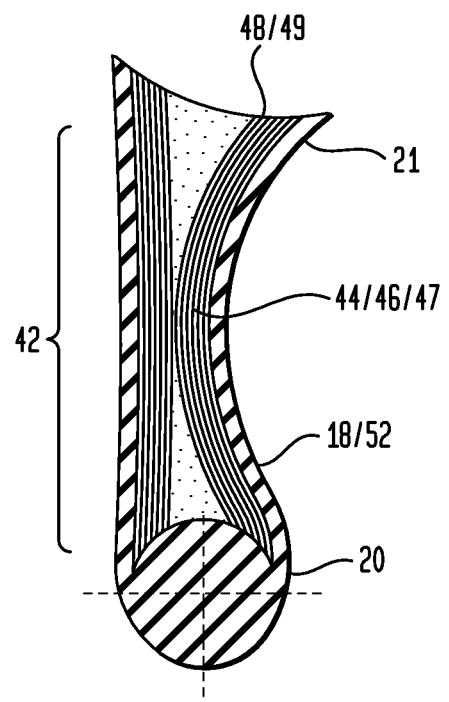
FIG. 11 is a cross section view 11-11 shown in FIG. 5 of a particular embodiment of a support member.
Figure 12A:
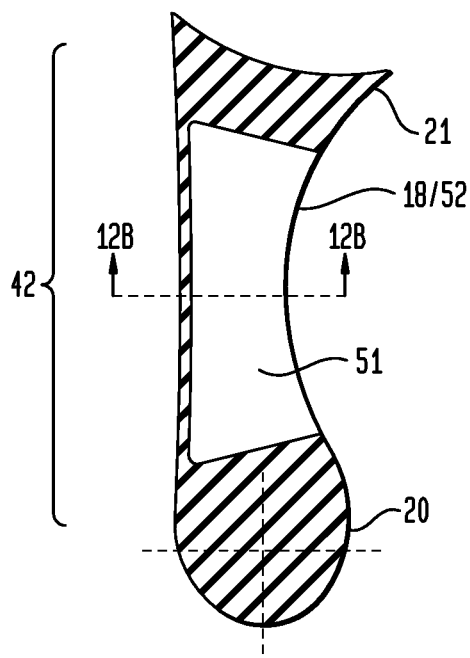
FIG. 12A is a cross section view 12A-12A shown in FIG. 5 of a particular embodiment of a support member.
Figure 12B:
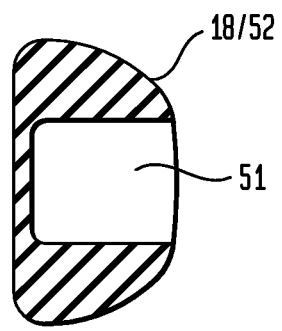
FIG. 12B is a cross section view 12B-12B shown in FIG. 12A of a particular 2embodiment of a support member.
Figure 13A:
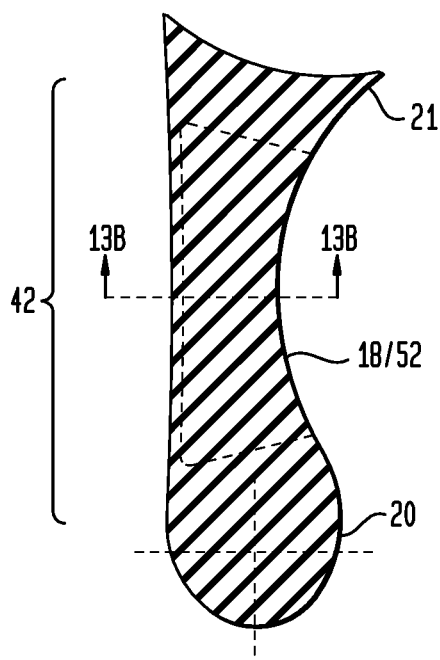
FIG. 13A is a cross section view 13A-13A shown in FIG. 5 of a particular embodiment of a support member.
Figure 13B:
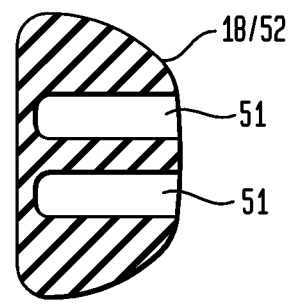
FIG. 13B is a cross section view 13B-13B shown in FIG. 13A of a particular embodiment of a support member.
Figure 14A:
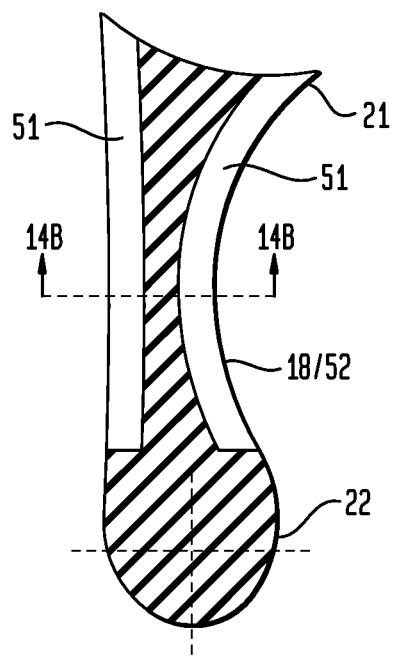
FIG. 14A is a cross section view 14A-14A shown in FIG. 5 of a particular embodiment of a support member.
Figure 14B:
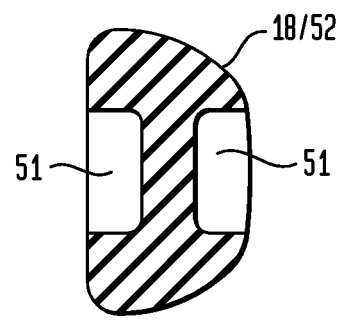
FIG. 14B is a cross section view 14B-14B shown in FIG. 14A of a particular embodiment of a support member.

Now referring primarily to FIGS. 10 and 11, particular embodiments of the support member (18) can further include a reinforcement element (44) disposed inside of the support member (18). The reinforcement element (44) can take the form of an elongate reinforcement member (45) (as shown in the example of FIG. 10) which can be produced from a metal, plastic, carbon fiber, resin impregnated fiberglass, or the like, or can take the form of a laminate member (46) constructed by uniting two or more layers (47) of laminatable material (48) together by the application of sufficient amounts of heat and pressure. The layers of laminatable material (48) can be the same, similar, or different as to composition of material. The layers (47) of laminatable material (48) can be in the form of sheets, which can be obtained as woven or non-woven materials such as: boron carbide, silicon carbide, alumina, alumina titanium, carbon, a para-aramid fiber such as KEVLAR, polypropylene such as INNEGRA available from Innegra Technologies, a ultra-high molecular weight polyethylene such as DYNEEMA or SPECTRA, s-glass, e-glass, or the like. An amount of adherent material (49) can be disposed between the layers of laminatable material (48) such as phenolic, epoxy, polyethylene terephtalate, vinylester, polyimides, bis(maleimide/diallybisphenol A, cyanate esters, thermoplastics, polypropyelene, nylon, or the like.

Figure 15:
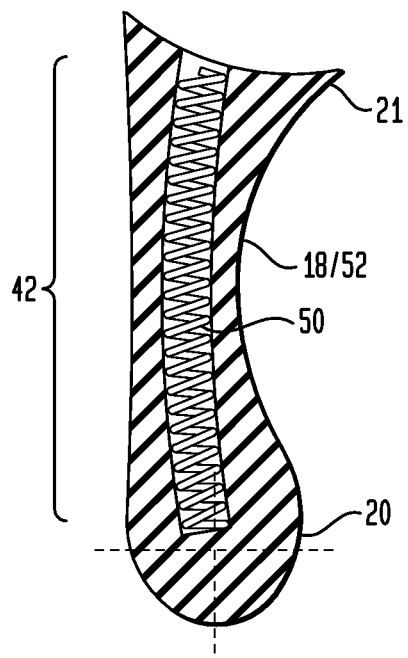
FIG. 15 is a cross section view 15-15 shown in FIG. 5 of a particular embodiment of a support member.

Now referring primarily to FIG. 15, particular embodiments of the support member (18) can further include a spring element (50) disposed inside of the support member (18) and as to particular embodiments the spring element (50) can comprise a coil spring.

Now referring primarily to FIGS. 12A and 12B, 13A and 13B, and 14A and 14B, the medial portion (42) can include recess elements (51) which function to reduce the amount of elastomeric material (52) and to adjust the amount of resilient flexure (43) or the alter the flexural modulus of how the support member (18) will deform and strain in response the mass of the ball (2) retained in the ball handling structure (12).

Again referring primarily to FIGS. 4 through 8, a ball handling structure (12) couples to the support second end (21) of the support member (18). The ball handling structure (12) can have an external surface (53) and an internal ball handling surface (22). The ball handling structure (12) will typically be fabricated or formed from an elastomer material (52) as above described to afford an amount of resilient flexure (54) in the ball handling structure (12); however, particular embodiments can also be formed from a substantially inflexible material such as a cross-linked polyethylene, polystyrene, acrylonitrile-butadeien-styrene, metal, or the like.

While the external surface (53) of the ball handling structure (12) can be configured as a partial spherical surface as shown in the examples of FIGS. 4 through 8; the invention is not so limited, and the external surface (53) of the ball handling structure (12) can be configured in a wide variety of forms to afford a desired appearance. The ball handling surface (22) defines the ball receiving cavity (11) and an opening (14) through which the ball (2) passes to be located within the ball receiving cavity (11). Typically, the ball handling surface (22) has a configuration which engages the ball external surface (55). As shown in the example of FIG. 2, the ball handling surface (22) can be configured as spherical surface (56) to receive a spherical ball such as a baseball. The spherical surface (56) can have a radius similar to the radius of the spherical ball (2). As to certain embodiments, the spherical surface (56) can extend beyond the ball midline (57) and the ball handling structure (12) can be sufficiently resiliently flexible to allow the ball (2) to pass through the opening (14) into the ball receiving cavity (11).

Figure 4:
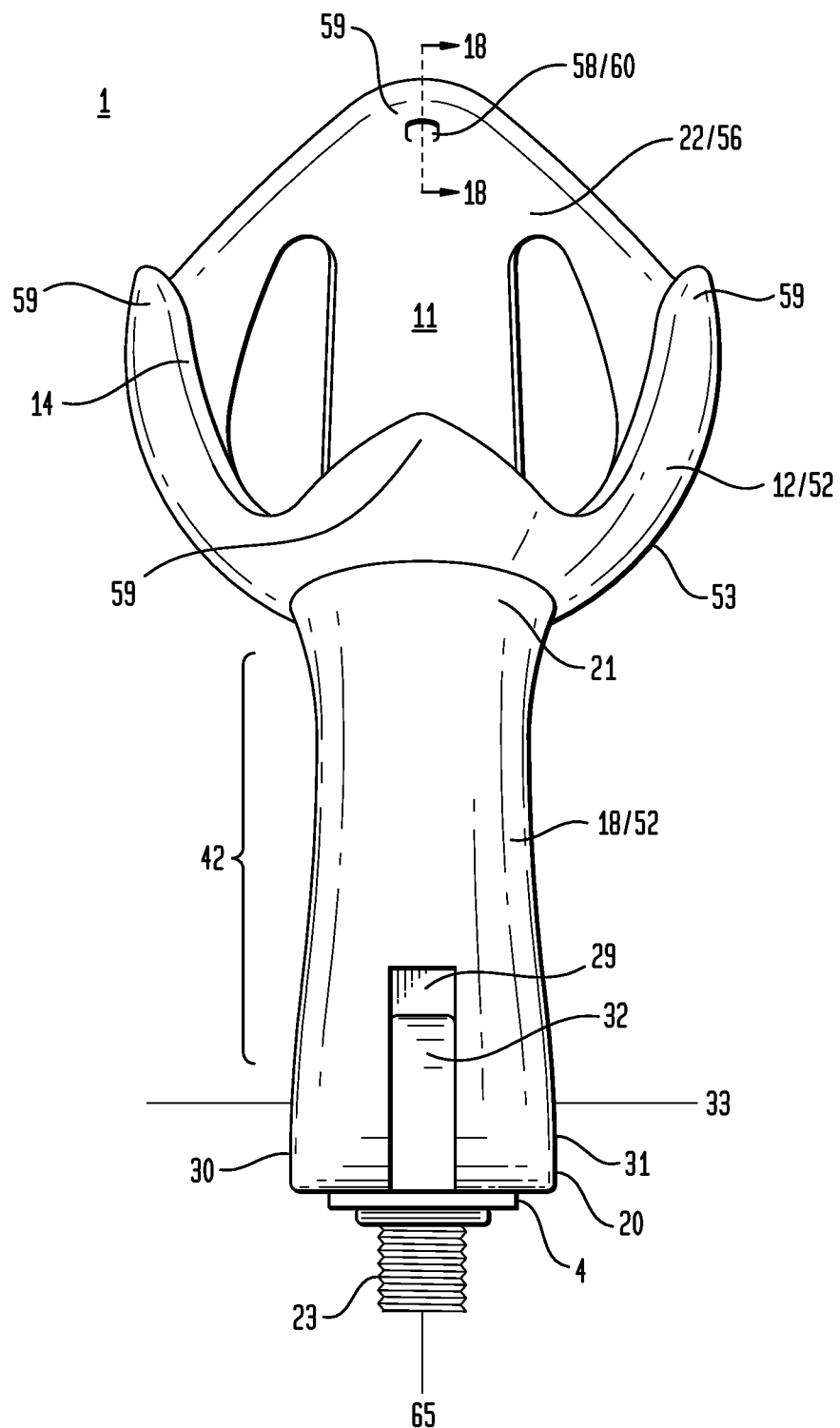
FIG. 4 is a front view of a particular embodiment of the inventive prosthetic device for handling a ball.
Figure 5:
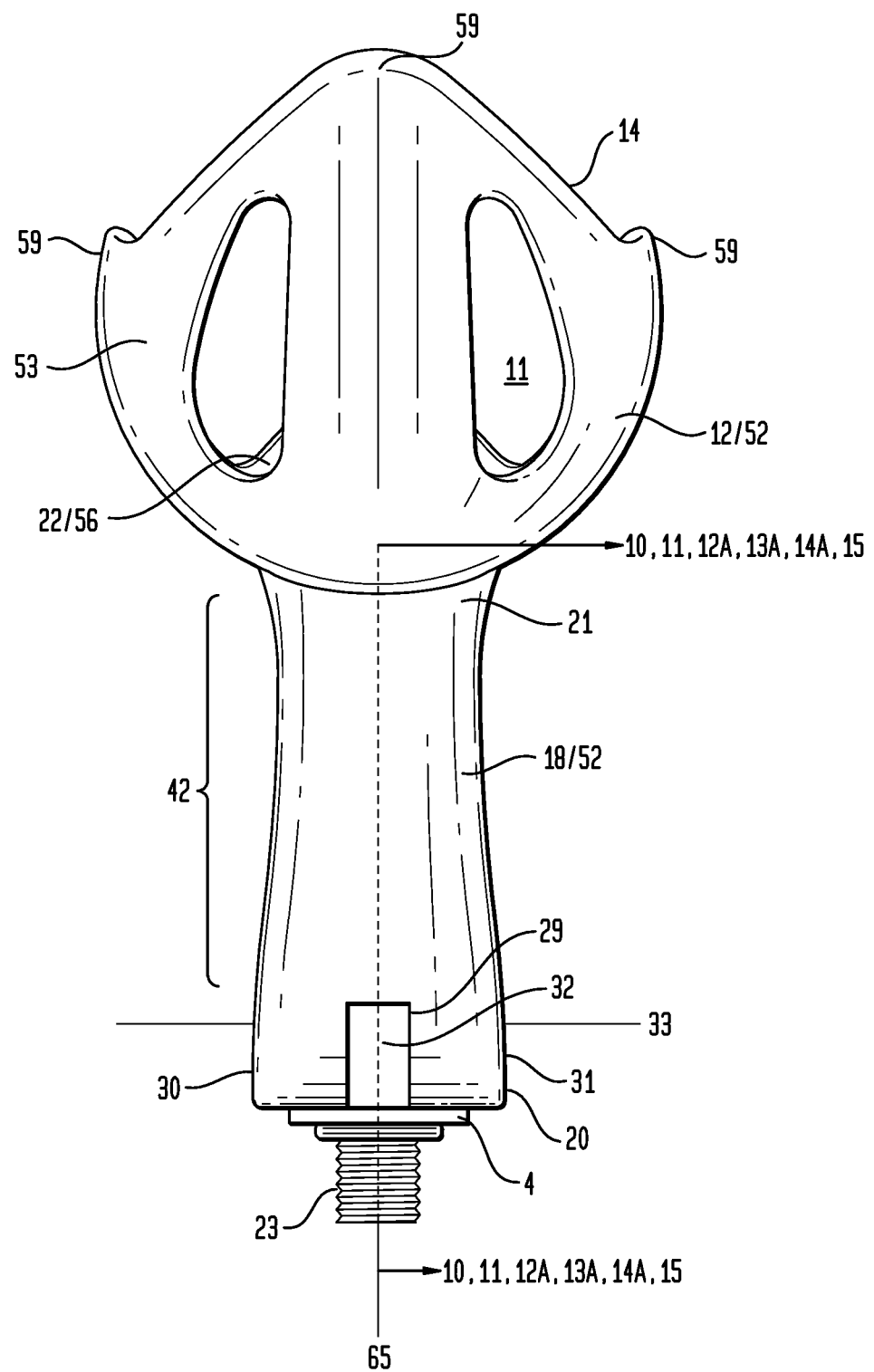
FIG. 5 is a back view of a particular embodiment of the inventive prosthetic device for handling a ball.
Figure 6:
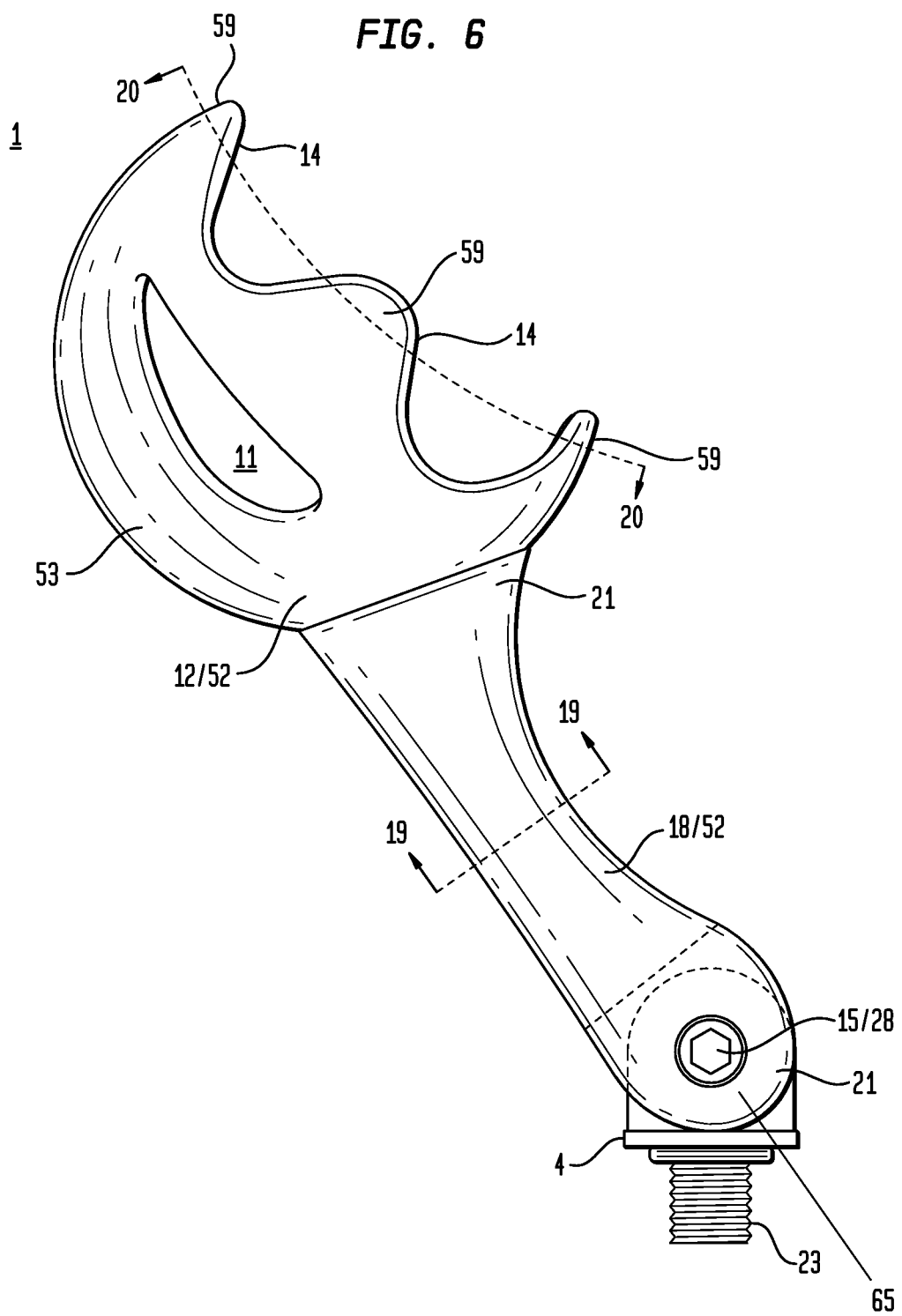
FIG. 6 is a side view of a particular embodiment of the inventive prosthetic device for handling a ball.
Figure 7:
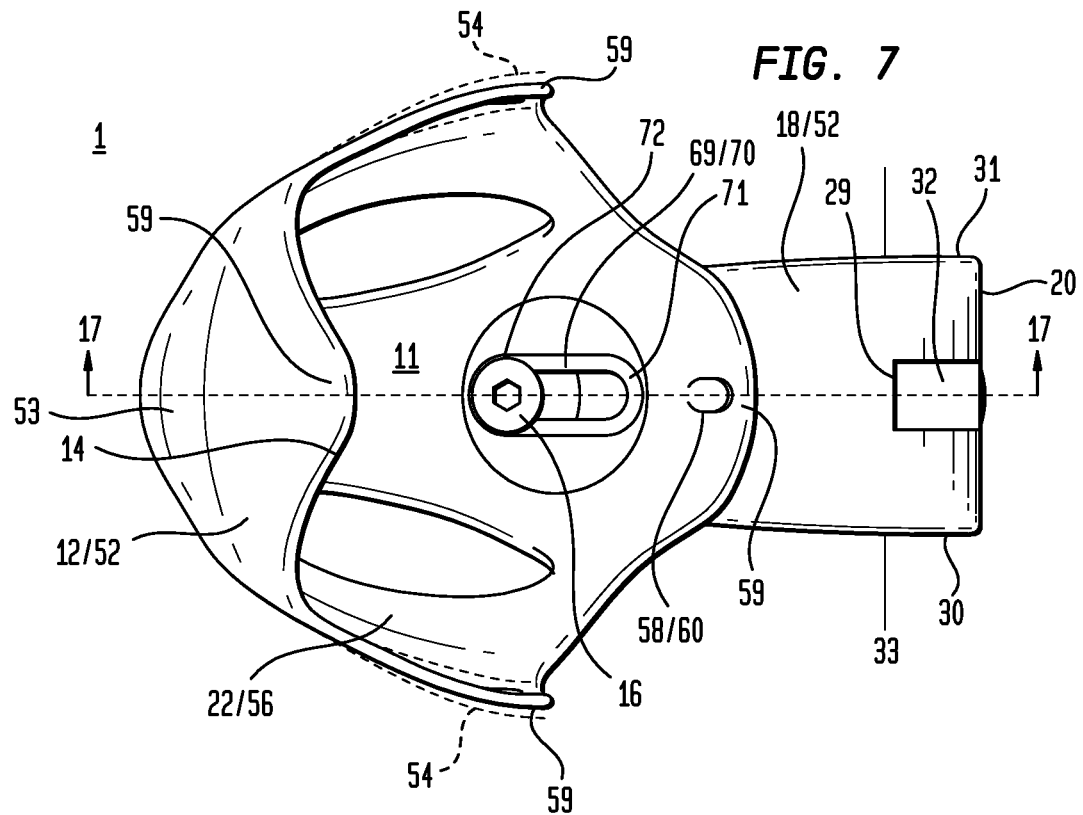
FIG. 7 is a top view of a particular embodiment of the inventive prosthetic device for handling a ball.
Figure 8:
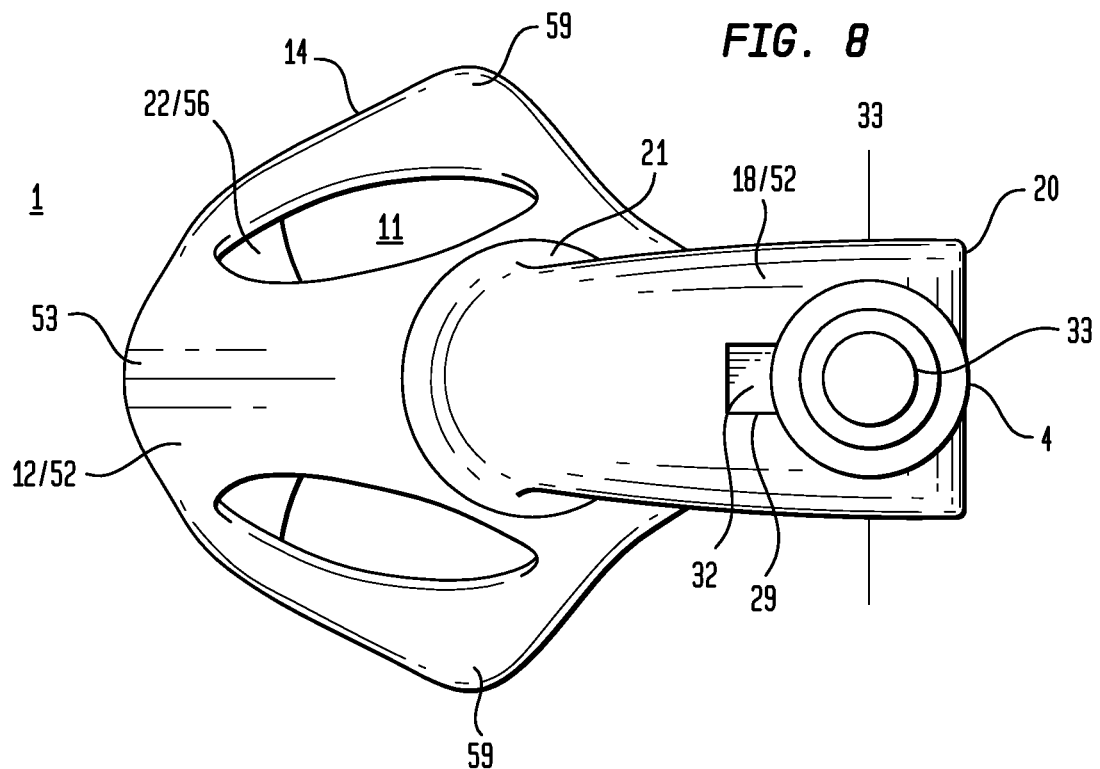
FIG. 8 is a bottom view of a particular embodiment of the inventive prosthetic device for handling a ball.

Now referring primarily to FIGS. 2, 4, and 7, certain embodiments include one or more ball retention elements (58) coupled to the ball handling surface (22) proximate the opening (14). As shown in the example of FIGS. 4 and 7, a pair of ball retention elements (58) can be disposed in opposed relation proximate the opening (14). The ball retention elements (58) can project a distance outward of the ball handling surface (22) to locate a pair of retention surfaces (59)(60) at a lesser distance apart than the diameter of the ball (2). The ball handling structure (12) can be sufficiently resiliently flexible to allow the ball (2) to pass over the one or more ball retention elements (58) and into the ball receiving cavity (11). As to certain embodiments, the ball handling structure (12) can further include one or more tangs (59) (projections) which extend portions of the ball handling structure (12) and correspondingly the ball handling surface (22) beyond the ball midline (57) receivable inside the ball receiving cavity (11). The one or more ball retention elements (58) can be correspondingly coupled to the one or more tangs (59) to locate the ball retention elements (58) beyond the ball midline (57). The one or more tangs (59) can be sufficiently resiliently flexible to allow the ball (2) to pass over the one or more ball retention elements (58) and into the ball receiving cavity (11).

Now referring primarily to FIG. 18, particular embodiments of the ball retention elements (58) can in relation to the ball handling surface (22) increase in height approaching the opening (14) of the ball handling structure (12) with certain embodiments providing an inclined retention surface (60) which commences at the ball handling surface (12) and extends inwardly to a height which restricts the opening (14) in a least one dimension to necessitate resilient flexure of the ball handling structure (12) to allow the ball (2) to pass into or out of the ball receiving cavity (11).

Now referring primarily to FIG. 20, as to particular embodiments, the ball retention elements (58) can take the form of one or more spring loaded detents (61) each including a detent bore (62) in the ball handling structure (12) having an detent aperture (62) disposed in the ball handling surface (22) of lesser dimension than a detent element (63) movably engaged within the detent bore (62) such that a portion of the detent element (63) extends a distance into the ball receiving cavity (11). A detent spring (64) can engage the detent element (63) to forcibly urge a portion to extend into the ball receiving cavity (11). A ball (2) can engage the portion of the detent element (63) extending into the ball receiving cavity (11) with sufficient force to compress the detent spring (64) to dispose the detent element (63) sufficiently flush with the ball handling surface (22) to allow the passage of the ball (2) into or out of the ball receiving cavity (11).

Figure 17:
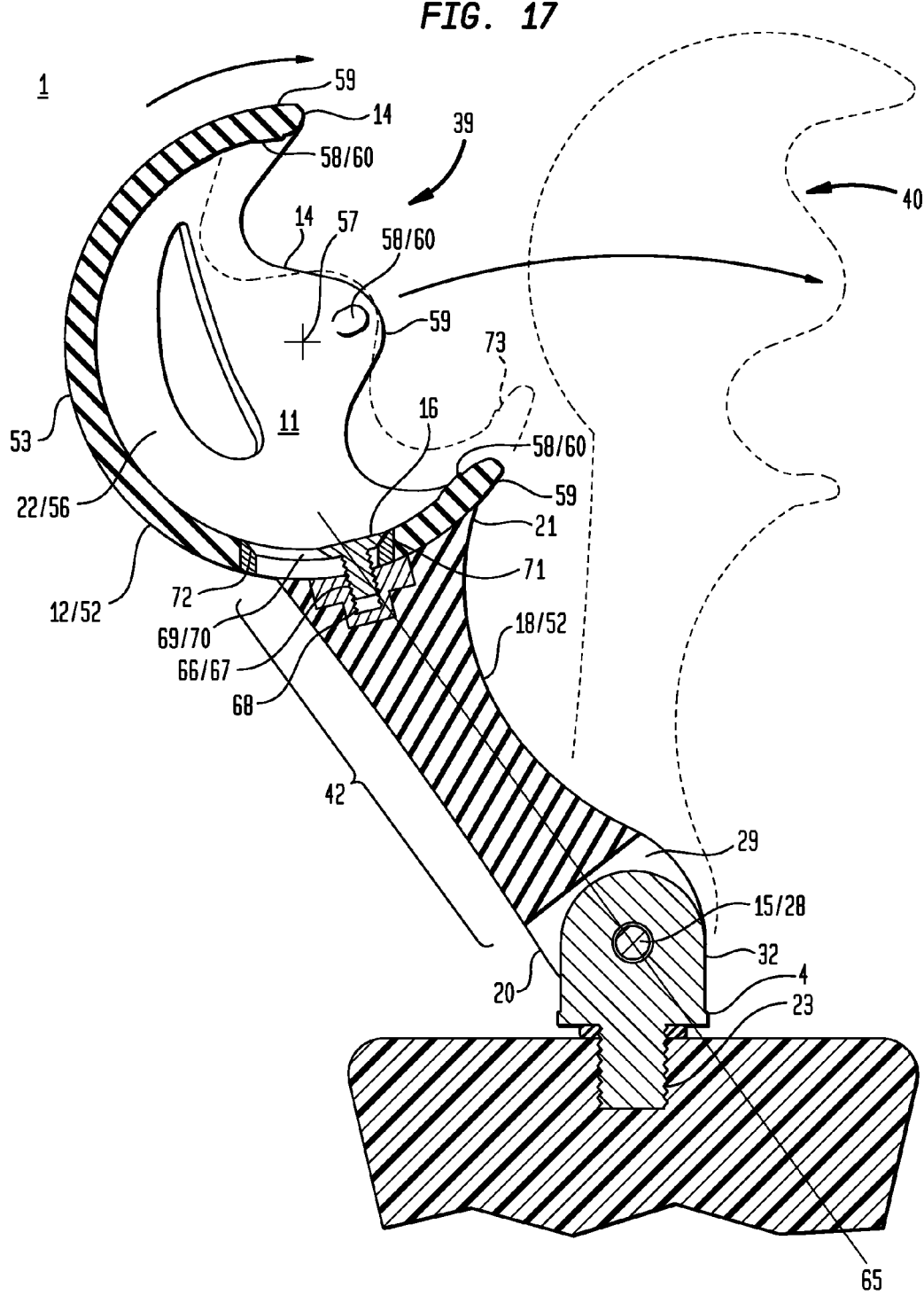
FIG. 17 is cross section view 17-17 shown in FIG. 7 of a particular embodiment of a support member.

Now referring primarily to FIGS. 7 and 17, embodiments of the ball handling structure (12) can further include a second pivot element (16) which allows the opening (14) of the ball handling structure (12) to rotate radially about the central longitudinal axis (65) of the support member (18). The particular embodiment of the second pivot element (16) shown in the example of FIG. 17 includes a second pivot shaft (66) with a spiral thread (67) which rotatingly engages a second pivot threaded recess (68) in the support second end (21). The ball handling structure (12) can further include an aperture element (69) through which the second pivot shaft (66) passes allowing the opening (14) of the ball handling structure (12) to be radially rotated about the second pivot shaft (66) and by operation of the spiral thread (67) in the second pivot threaded recess (68) the external surfaces of the support second end (21) and the ball handling structure (12) can be engaged in fixed relation.

Now referring primarily to FIGS. 7 and 17, as to particular embodiments of the ball handling structure (12) the aperture element (69) can take the form of an elongate slot (70) in which the second pivot shaft (66) can be positioned at a location between a slot first end (71) (as shown in the example of FIG. 7) and a slot second end (72) (as shown in the example of FIG. 17) which allows the opening (14) of the ball handling structure (12) to rotate radially about the central longitudinal axis (65) of the support member (18) and further allows the pitch (73) of the opening (14) to be adjusted in relation to the central longitudinal axis (65) of the support member (18).

As can be easily understood from the foregoing, the basic concepts of the present invention may be embodied in a variety of ways. The invention involves numerous and varied embodiments of a prosthetic device for ball handling and methods for making and using such prosthetic device including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "supports" should be understood to encompass disclosure of the act of "supporting"—whether explicitly discussed or not—and, conversely, were there effectively disclosure of the act of "supporting", such a disclosure should be understood to encompass disclosure of a "support" and even a "means for supporting." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the prosthetic devices herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A method of producing a prosthetic device for handling a ball, comprising:
   a) providing an attachment portion configured to couple said prosthetic device to an amputee;
   b) pivotally coupling a support member having a length disposed between a support first end and a support second end to said attachment portion by said support first end allowing rotation of said support member about a first pivot element, said support member having a support lock which operates to fix orientation of said support member in relation to said attachment portion; and
   c) pivotally coupling a ball handling structure to said support second end, said ball handling structure having an aperture element through which a second pivot element passes to pivotally couple said ball handling structure to said support second end, said ball handling structure having a ball handling surface configured to engage a ball, said ball handling surface having an opening through which said ball can pass, said opening radially rotatable about a longitudinal axis of said support member by pivoting said ball handling structure about said second pivot element.

2. The method of claim 1, further comprising providing said ball handling surface in a generally spherical configuration.

3. The method of claim 1, further comprising coupling one or more ball retention elements to said ball handling surface proximate said opening.

4. The method of claim 3, further comprising providing said one or more ball retention elements in a configuration which in relation to said ball handling surface increase in height approaching said opening.

5. The method of claim 4, providing said ball handling structure with resilient flexure, said ball handling structure flexing to allow a ball to pass over said one or more ball retention elements to engage said ball handling surface.

6. The method of claim 4, further comprising providing said ball retention elements as one or more spring loaded detents.

7. The method of claim 1, further comprising providing one or more tangs which extend a distance into said opening.

8. The method of claim 7, further comprising extending at least one of said tangs a sufficient distance into said opening to engage said ball beyond a ball midline.

9. The method of claim 8, further comprising correspondingly coupling one more ball retention elements to said one or more tangs.

10. The method of claim 9, providing said ball handling structure with resilient flexure, said ball handling structure flexing to allow a ball to pass over said one or more ball retention elements to engage said ball handling surface.

11. The method of claim 9, further comprising providing said ball retention elements as one or more spring loaded detents.

12. The method of claim 1, further comprising providing support member with a medial portion resiliently flexible in response to movement of said ball handling structure.

13. The method of claim 12, further comprising coupling a spring element to said support member, said spring element responsive to resilient flexure of said support element.

14. The method of claim 13, further comprising locating said spring element within said support member.

15. The method of claim 14, further comprising selecting said spring element from the group consisting of: a coil spring, a carbon rod, a fiberglass rod, and a laminated member.

16. The method of claim 1, further comprising correspondingly coupling opposed ends of a spring element to said support member and to said attachment portion, said spring element responsive to rotation of said support member in relation to said attachment portion.

17. The method of claim 16, further comprising coupling a spring tensioner to said spring element which allows variable adjustment of tension in said spring element.

18. The method of claim 1, wherein said aperture element defines an elongate slot through which said second pivot element passes which allows said opening to radially rotate about the longitudinal axis of said support member, and further comprising adjusting position of said pivot element in said elongate slot to change pitch of said opening in relation to said longitudinal axis of said support member.

19. The method of claim 1, further comprising providing a medial portion of said support member in a configuration having two or more discrete support elements joined proximate said support first end and said support second end.

* * * * *